(12) United States Patent
Tsubouchi

(10) Patent No.: US 11,318,238 B2
(45) Date of Patent: May 3, 2022

(54) BLOOD INSPECTION SYSTEM AND BLOOD INSPECTION CONTROL METHOD

(71) Applicant: TERUMO KABUSHIKI KAISHA, Tokyo (JP)

(72) Inventor: Takeshi Tsubouchi, Ann Arbor, MI (US)

(73) Assignee: Terumo Kabushiki Kaisha, Tokyo (JP)

( * ) Notice: Subject to any disclaimer, the term of this patent is extended or adjusted under 35 U.S.C. 154(b) by 703 days.

(21) Appl. No.: 16/181,684

(22) Filed: Nov. 6, 2018

(65) Prior Publication Data

US 2019/0070352 A1    Mar. 7, 2019

Related U.S. Application Data

(63) Continuation of application No. PCT/JP2017/015798, filed on Apr. 19, 2017.

(30) Foreign Application Priority Data

May 18, 2016   (JP) .............................. JP2016-099755

(51) Int. Cl.
*A61B 5/00*       (2006.01)
*A61M 1/36*       (2006.01)
(Continued)

(52) U.S. Cl.
CPC ......... *A61M 1/3609* (2014.02); *A61B 5/1473* (2013.01); *A61B 5/157* (2013.01);
(Continued)

(58) Field of Classification Search
CPC .............. A61M 1/3609; A61M 39/223; A61M 1/3666; A61B 5/150992; A61B 5/157;
(Continued)

(56) References Cited

U.S. PATENT DOCUMENTS

| 5,302,348 A | 4/1994 | Cusack et al. |
| 5,335,658 A | 8/1994 | Bedingham |

(Continued)

FOREIGN PATENT DOCUMENTS

| EP | 3459460 A1 | 3/2019 |
| JP | 6176341 U  | 5/1986 |

(Continued)

OTHER PUBLICATIONS

International Search and Opinion Report for PCT/JP2017015798, dated Jul. 4, 2017.

(Continued)

*Primary Examiner* — May A Abouelela
(74) *Attorney, Agent, or Firm* — MacMillan, Sobanski & Todd, LLC

(57) ABSTRACT

A blood inspection system automatically repeats blood inspections at a plurality of times at a desired interval and a desired timing by chronologically coupling a supply of blood to each one of a series of blood inspection units. A change in a blood condition, such as a clotting time, is monitored so that a thrombus or the like is prevented from being formed and an associated medicine is prevented from being overdosed. The blood inspection system has a catheter providing a main flow path, a supply of a flushing liquid, a plurality of inspection units, a plurality of branched flow paths, an aspiration unit, and a switching valve for selectively coupling the main flow path to a determined inspection unit which has not yet performed an inspection.

7 Claims, 6 Drawing Sheets

(51) Int. Cl.
 A61B 5/157 (2006.01)
 A61B 5/1473 (2006.01)
 A61B 5/15 (2006.01)
 A61M 39/22 (2006.01)
 B08B 9/032 (2006.01)
 G01N 33/49 (2006.01)

(52) U.S. Cl.
 CPC ..... A61B 5/150992 (2013.01); A61M 1/3666 (2013.01); A61M 39/223 (2013.01); B08B 9/032 (2013.01); G01N 33/4905 (2013.01); *B08B 2209/032* (2013.01)

(58) Field of Classification Search
 CPC ................ A61B 5/1473; A61B 5/6852; A61B 5/150229; A61B 5/150221; A61B 5/15003; A61B 5/02035; A61B 5/155; B08B 9/032; B08B 2209/032; G01N 33/4905
 USPC .................................. 600/369, 573, 576, 583
 See application file for complete search history.

(56) References Cited

U.S. PATENT DOCUMENTS

| | | | |
|---|---|---|---|
| 5,399,497 A * | 3/1995 | Kumar | B01F 13/0809 422/68.1 |
| 5,662,107 A * | 9/1997 | Sakariassen | G01N 33/4905 600/369 |
| 5,758,643 A | 6/1998 | Wong et al. | |
| 5,777,221 A * | 7/1998 | Murthy | G01F 1/7086 250/577 |
| 8,783,121 B2 | 7/2014 | Hashizume et al. | |
| 10,286,149 B2 * | 5/2019 | Velschow | A61B 5/150229 |
| 2003/0114785 A1 | 6/2003 | Kikuchi et al. | |
| 2007/0179435 A1 * | 8/2007 | Braig | A61B 5/14546 604/66 |
| 2007/0191735 A1 * | 8/2007 | Hansson | A61B 5/15003 600/573 |
| 2007/0212784 A1 | 9/2007 | Okun | |
| 2008/0015487 A1 * | 1/2008 | Szamosfalvi | A61M 1/3658 604/6.07 |
| 2009/0131861 A1 * | 5/2009 | Braig | A61B 5/155 604/66 |
| 2010/0121170 A1 * | 5/2010 | Rule | A61B 5/14532 600/365 |
| 2010/0145175 A1 * | 6/2010 | Soldo | A61B 5/14532 600/365 |
| 2011/0092784 A1 * | 4/2011 | Butler | A61B 5/150221 600/322 |
| 2011/0098597 A1 | 4/2011 | Wu et al. | |
| 2011/0313317 A1 * | 12/2011 | Callicoat | A61B 5/412 600/581 |
| 2011/0313318 A1 * | 12/2011 | Rule | A61B 5/4839 600/581 |
| 2012/0078137 A1 * | 3/2012 | Mendels | G01F 23/2921 600/584 |
| 2012/0123298 A1 * | 5/2012 | Mendels | A61B 5/150946 600/579 |
| 2012/0203089 A1 * | 8/2012 | Rule | A61B 5/150213 600/366 |
| 2014/0012097 A1 * | 1/2014 | McCrea | A61B 5/14542 600/301 |
| 2014/0364765 A1 * | 12/2014 | Callaghan | A61M 1/3659 600/581 |
| 2014/0364766 A1 * | 12/2014 | Devgon | A61B 5/150221 600/581 |
| 2015/0198501 A1 * | 7/2015 | Rule | A61B 5/15087 73/40.5 R |
| 2016/0029934 A1 | 2/2016 | Hashizume et al. | |
| 2016/0029998 A1 * | 2/2016 | Brister | A61B 1/041 600/424 |
| 2016/0296690 A1 * | 10/2016 | Kume | A61M 1/3613 |
| 2017/0020428 A1 * | 1/2017 | Rogers | A61B 5/154 |
| 2018/0110916 A1 * | 4/2018 | Xue | G01N 33/492 |

FOREIGN PATENT DOCUMENTS

| | | |
|---|---|---|
| JP | 06000173 A | 11/1994 |
| JP | 2001116666 A | 4/2001 |
| JP | 2015206608 A | 11/2015 |
| WO | 2014033798 A1 | 6/2014 |

OTHER PUBLICATIONS

Extended European Search Report for EP17799102.3, dated Jan. 8, 2020.

JPO Office Action, JP2018-518170, dated Aug. 18, 2020.

* cited by examiner

BLOOD INSPECTION SYSTEM AND BLOOD INSPECTION CONTROL METHOD

CROSS REFERENCE TO RELATED APPLICATIONS

This application is a continuation of PCT Application No. PCT/JP2017/015798, filed Apr. 19, 2017, based on and claiming priority to Japanese Application No. 2016-099755, filed May 18, 2016, both of which are incorporated herein by reference in their entirety.

BACKGROUND OF THE INVENTION

The present invention relates to a blood inspection system and a control method for a blood inspection system.

In the related art, treatment has been performed by a percutaneous cardiopulmonary support (PCPS) method for cardiopulmonary resuscitation, circulation support, respiratory support in emergency treatment. This percutaneous cardiopulmonary support method is a method of temporarily supporting and substituting for a cardiopulmonary function in extracorporeal circulation.

In treatment accompanying extracorporeal circulation of artificial heart and lung, or the like, since blood is in an environment likely to be in contact with foreign bodies such as air, activated blood is likely to clot and form a thrombus. Therefore, a thrombus is inhibited from being formed by giving a dose of an anticoagulant such as heparin into blood during treatment. On the other hand, if an anticoagulant is overdosed, it may cause metrorrhagia, cerebral hemorrhage, and the like. Therefore, it is desirable that the degree of inhibition of blood clotting is inspected by performing a blood clotting inspection and the dosage of the anticoagulant is adjusted based on the result thereof.

Examples of a method for a blood clotting inspection include a method of measuring an activated clotting time (ACT), in which an inspection result can be obtained in a comparatively simple manner in a short time. According to a method of measuring an activated clotting time, an index of the readiness of blood to clotting can be obtained by measuring a clotting time of blood which is activated due to an added clotting accelerator.

For example, U.S. Pat. No. 5,302,348 discloses a method of measuring an activated clotting time, in which a clotting accelerator is added to blood disposed in a thin tube-shaped test tube, the blood is caused to flow in the test tube, and flow characteristics thereof are observed.

Since an activated clotting time of blood changes from moment to moment, the activated clotting time needs to be repeatedly measured a plurality of times during treatment. If the activated clotting time is manually measured by a person, the processing time may be slow and deviations may occur during the interval between measurement times, so that it may not be possible to accurately and quickly recognize a change in the activated clotting times. In addition, after blood has clotted inside one particular test tube used for a particular measurement of the activated clotting time, the test tube needs to be replaced with another test tube for a next measurement. Therefore, each test tube can only be used to perform a single measurement in the prior art.

In addition, blood inspections required for treatment are not limited to a clotting inspection. For example, it may be desirable to inspect for concentration of a component in blood, such as glucose. Similarly, in such a component inspection in blood as well, it is desirable for a chronological change to be measured and a dosage of a medicine such as insulin to be adjusted based on the result thereof.

SUMMARY OF THE INVENTION

An object of the present invention is to provide a blood inspection system and control method, in which a condition of a patient can be chronologically measured by automatically repeating blood inspections a plurality of times at a desired interval and a desired timing and measuring a chronological change in a blood condition, so that a thrombus or the like is prevented from being formed and a medicine is prevented from being overdosed.

In order to achieve the above object, there is provided a blood inspection system for inspecting blood. The blood inspection system includes a main flow path through which a fluid including blood circulates, a supply section which supplies a cleaning/flushing liquid to the main flow path, a plurality of inspection units which perform a blood inspection, a plurality of branched flow paths which are bifurcated from the main flow path and which guide blood to the plurality of inspection units, an aspiration unit which aspirates (i.e., pumps) blood from a living body via the main flow path and guides the blood to the plurality of branched flow paths, a discharge flow path which communicates with the main flow path and discharges at least apart of the fluid from the main flow path and/or the plurality of branched flow paths, a switching unit/valve which is capable of selectively coupling the main flow path to any one of the plurality of bifurcated flow paths or to the discharge flow path, and a control unit which controls an operation of each of the units of the system. The control unit causes the main flow path and a determined one of the branched flow paths of the plurality of branched flow paths to communicate with each other when performing a blood inspection using a determined one of the plurality of inspection units such that blood is guided to the determined one inspection unit of the plurality of inspection units, being one which has not yet performed an inspection.

In order to achieve the above object, there is provided a control method for a blood inspection system controlling a supply section which supplies a cleaning liquid to a main flow path, a plurality of inspection units which perform a blood inspection, an aspiration unit which aspirates blood from a living body and which guides the blood to a plurality of bifurcated flow paths bifurcated from the main flow path, and a switching unit which is capable of switching between a communication state of the main flow path and a selected one of the plurality of bifurcated flow paths or a communication state of the main flow path and a discharge flow path capable of discharging a fluid. The control method includes a cleaning step of cleaning an inside of the main flow path by discharging a fluid from the main flow path while supplying the cleaning liquid to the main flow path, an inspecting step of inspecting blood using one inspection unit of the plurality of inspection units by causing the main flow path and one bifurcated flow path of the plurality of bifurcated flow paths to communicate with each other, and another inspecting step of inspecting blood using another inspection unit of the plurality of inspection units, which has not yet performed an inspection.

According to the blood inspection system and the control method for a blood inspection system having the configurations as described above, it is possible to perform control in which an inspection is performed by selecting one inspection unit from inspection units which have not yet performed an inspection. Through the control, blood inspections can be automatically repeated a plurality of times at a desired interval and a desired timing. Therefore, it is possible to measure a chronological change in a blood condition such as an activated clotting time. In addition, an inspection unit of single use can be used for each one of the plurality of automatic inspections. Therefore, it is possible to perform an inspection more simply in a short time. Accordingly, it is possible to reduce a load to a patient by preventing a thrombus or the like from being formed and preventing a medicine such as an anticoagulant from being overdosed.

DESCRIPTION OF PREFERRED EMBODIMENTS

Hereinafter, with reference to the accompanying drawings, embodiments of the present invention will be described. The following description does not limit the technical scope or meaning of the terms recited in the claims. In addition, for the convenience of description, there are cases where the dimensional ratios of the drawings are exaggerated and are different from the actual ratios.

First Embodiment

Figure 1:
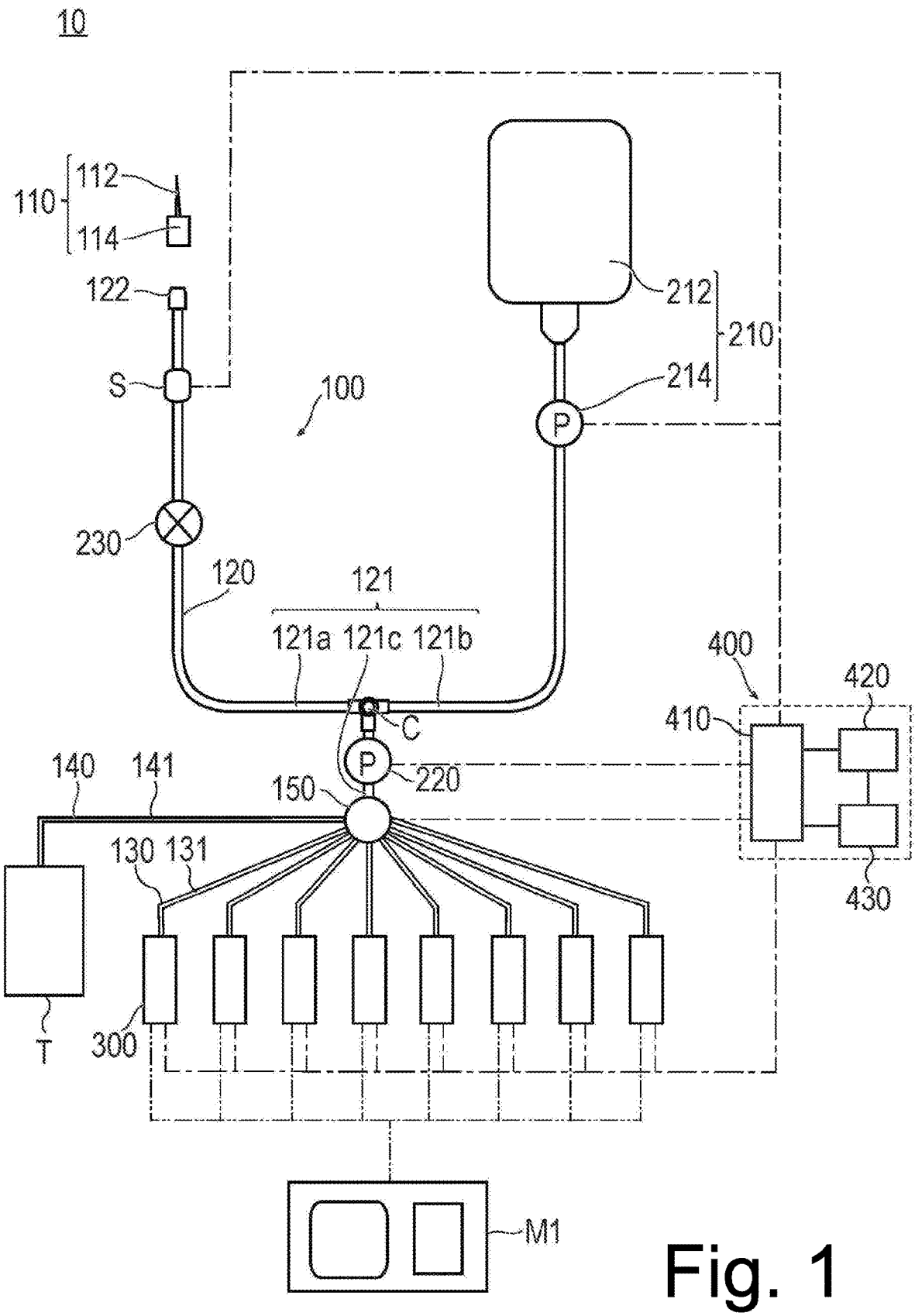
FIG. 1 is a view schematically illustrating the entirety of a blood inspection system according to a first embodiment.

With reference to FIG. 1, a blood inspection system 10 according to a first embodiment of the present invention will be described.

For example, the blood inspection system 10 according to the first embodiment obtains information for recognizing a blood condition by automatically performing blood inspections at a predetermined interval when performing a surgery while supporting lungs or the heart using an artificial heart-lung apparatus. The present embodiment shows, as an example of a blood inspection, a clotting inspection for measuring an activated clotting time (ACT) (which will hereinafter be simply referred to as a "clotting time").

As illustrated in FIG. 1, the blood inspection system. 10 includes a catheter 100 that forms a passage in which a fluid such as blood or a flushing liquid (corresponding to a cleaning liquid) circulates, a supply section 210 that supplies the flushing liquid to the catheter 100, an aspiration pump (corresponding to an aspiration unit) 220 that aspirates the fluid, a valve 230 that switches a flowing direction of the fluid, a plurality of inspection units 300 that perform a clotting inspection of blood, and a control unit 400 that controls an operation of each of the units of the blood inspection system 10. The blood inspection system 10 further includes a sensor S that measures the concentration of blood included in a fluid inside the catheter 100, a bifurcated connector C that is disposed in the catheter 100, a waste liquid tank T that stores a discarded fluid, and a measuring device M1 that measures inspection results of the inspection units 300 and displays a measurement result. Hereinafter, the configuration of each of the units will be described.

The catheter 100 includes a blood collecting needle 110 that punctures a living body (e.g., entering into a blood vessel), a first tube 120 that is connected to a proximal side of the blood collecting needle 110 and forms a main flow path 121 for circulating a fluid, a second tube 130 that is bifurcated from the main flow path 121 and forms a plurality of branched/bifurcated flow paths 131 which guide blood to the inspection units 300, a third tube 140 that forms a discharge flow path 141 which discharges at least a part of a fluid from the main flow path 121, and a switching unit 150 that is capable of selectively switching between a communication state of the main flow path 121 and the plurality of bifurcated flow paths 131 and a communication state of the main flow path 121 and the discharge flow path 141.

The blood collecting needle 110 has a hollow needle 112 which punctures a blood vessel, and a blood collecting needle hub 114 which is disposed on the proximal side of the needle 112. The needle 112 has a sharp needle tip at a distal end. For example, the blood collecting needle 110 can be formed of a metal or a resin material.

The first tube 120 includes a connection section 122 which can be connected to the blood collecting needle hub 114. For example, the first tube 120, the second tube 130, and the third tube 140 can be formed of a known resin, such as urethane, polyurethane, silicon, or vinyl chloride.

In a state where the first tube 120 and the blood collecting needle hub 114 are connected to each other via the connection section 122, the main flow path 121 constitutes a flow path through which a fluid can circulate among the blood collecting needle 110, a flushing liquid holding unit 212 of the supply section 210 (which will be described below), and the switching unit 150.

The main flow path 121 has a first main flow path 121a which communicates with the blood collecting needle 110, and a second main flow path 121b and a third main flow path 121c which are bifurcated from the first main flow path via the bifurcated connector C. The second main flow path 121b communicates with the flushing liquid holding unit 212 of the supply section 210. The third main flow path 121c communicates with the switching unit 150.

The bifurcated flow paths 131 and the discharge flow path 141 are bifurcated from the third main flow path 121c of the main flow path 121. The switching unit 150 is disposed between the third main flow path 121c, and the bifurcated flow paths 131 and the discharge flow path 141.

The bifurcated flow paths 131 cause the inspection units 300 to selectably communicate with the third main flow path 121c via the switching unit 150. A plurality of the bifurcated flow paths 131 are provided as many as the number of the inspection units 300. One bifurcated flow path 131 communicates with one inspection unit 300. In the present embodiment, there are provided eight bifurcated flow paths 131 and eight inspection units 300. The numbers of the bifurcated flow paths 131 and the inspection units 300 are not particularly limited and can be suitably changed in accordance with a desired number of times of inspections or the like.

The discharge flow path 141 causes the waste liquid tank T and the third main flow path 121c to communicate with each other via the switching unit 150.

The switching unit 150 includes a known switch valve such as an electromagnetic valve. The switching unit 150 alternatively selects one flow path from the plurality of bifurcated flow paths 131 or the discharge flow path 141, switching the one bifurcated flow path 131 or the discharge flow path 141 over to a state of communicating with the third main flow path 121c. Accordingly, the switching unit 150 guides a fluid, which has been guided to the third main flow path 121c, to the one bifurcated flow path 131 or the discharge flow path 141.

The supply section 210 includes the flushing liquid holding unit 212 which holds a flushing liquid, and a supply pump 214 which supplies a flushing liquid from the flushing liquid holding unit 212 to the catheter 100.

The flushing liquid holding unit 212 is a medical bag which holds a medical liquid such as a flushing liquid. For example, a physiological salt solution can be used as a flushing liquid.

The supply pump 214 is disposed in the second main flow path 121b and guides a flushing liquid, which has been supplied from the flushing liquid holding unit 212, toward the first main flow path 121a and the third main flow path 121c.

The aspiration pump 220 is disposed in the third main flow path 121c and guides a fluid from the first main flow path 121a or the second main flow path 121b toward the third main flow path 121c.

The valve 230 is disposed in the first main flow path 121a and is adapted to adjust the flowing direction or the flow rate of a fluid.

Figure 3A:
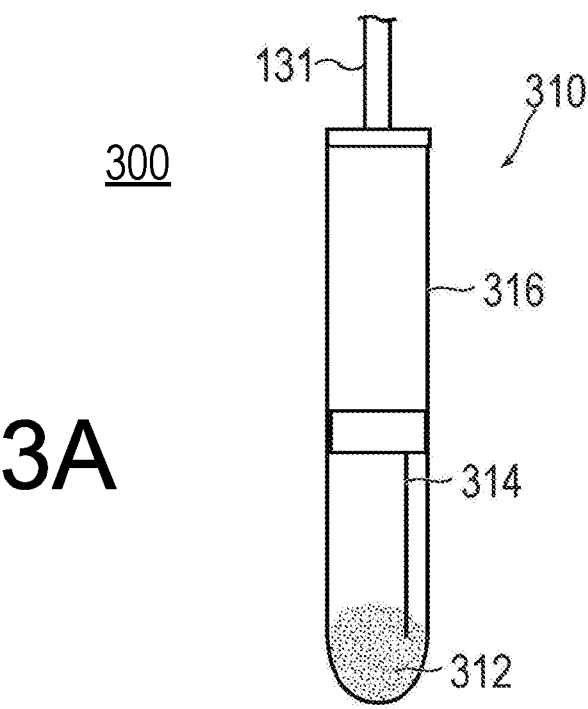
FIG. 3A is a schematic view illustrating an inspection unit according to the first embodiment.

The inspection units 300 perform a clotting inspection of blood guided from the bifurcated flow paths 131. As illustrated in FIG. 3A, the inspection unit 300 includes a clotting time measuring instrument 310 which measures the clotting time of blood. One respective clotting time measuring instrument 310 of the plurality of clotting time measuring instruments 310 is connected to one respective bifurcated flow path 131 of the plurality of bifurcated flow paths 131.

The clotting time measuring instrument 310 is a viscosity measuring module which measures the clotting time by measuring the viscosity of blood activated by mixing with a clotting accelerator. The clotting time measuring instrument 310 has a clotting accelerator substance 312 which accelerates clotting by activating blood, an inspection rod 314, and a test tube 316 which accommodates the clotting accelerator 312 and the inspection rod 314.

For example, silica, celite, kaolin, or glass can be used as the clotting accelerator 312. For example, an iron rod can be used as the inspection rod 314. For example, the test tube 316 is a slender container having a cylindrical shape of which an upper end is open.

For example, the sensor S includes a known light sensor including a light emitting element and a light receiving element. The sensor S is disposed in the first main flow path 121a and measures the concentration of blood included in a fluid inside the first main flow path 121a. When a blood inspection is performed, a threshold value for the concentration of blood is set in advance as a determination criterion for distinguishing between the cleaning state resulted from a flushing liquid inside the main flow path 121 or the replacement state resulted from blood. The threshold value includes a first threshold value which is a criterion for determining that the main flow path 121 is filled with a flushing liquid, and a second threshold value which is a criterion for determining that the main flow path 121 is filled with blood.

The second main flow path 121b and the third main flow path 121c are bifurcated from the first main flow path 121a at the bifurcated connector C. For example, the bifurcated connector C may include a T-connector.

Figure 3B:
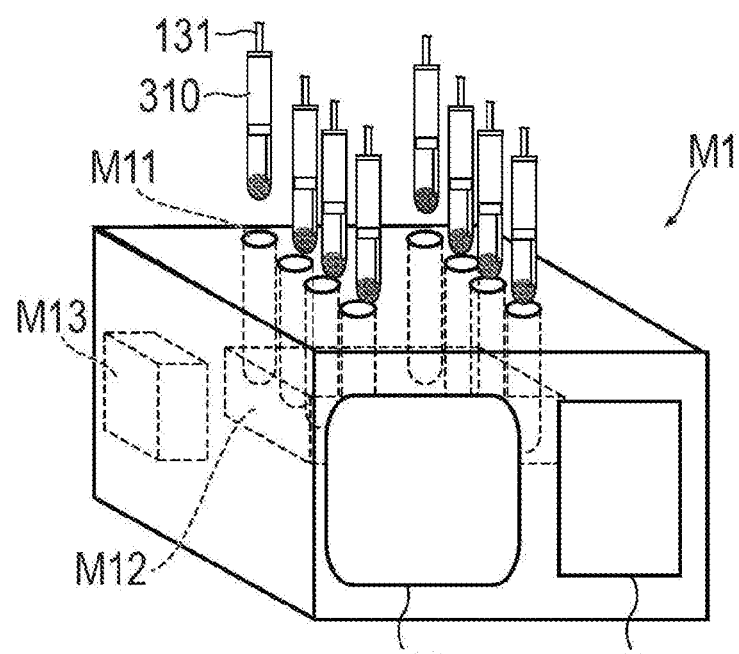
FIG. 3B is a schematic view illustrating a measuring device according to the first embodiment.

As illustrated in FIG. 3B, a known device can be used as the measuring device M1 serving as a clotting time measuring device which measures the clotting time of blood. The measuring device M1 according to the present embodiment includes a plurality of test tube holding portions M11 which hold the test tubes 316 of the plurality of clotting time measuring instruments 310 at measurement positions, a drive unit M12 which drives the test tubes 316 for a rotary movement thereof, a detection unit M13 which detects a movement of the inspection rods 314, a display unit M14 which displays a measurement result, and an operation unit M15 with which a practitioner performs a predetermined input operation.

The control unit 400 (FIG. 1) includes an input/output portion 410, a storage unit 420, and a computation portion 430, and the portions are connected to each other via an electric wiring or the like for receiving and transmitting a signal.

The input/output portion 410 is connected to each of the switching unit 150, the supply pump 214, the aspiration pump 220, the inspection units 300, and the sensor S. The storage unit 420 includes a ROM or a RAM, in which pieces of data such as an initial supply pressure of the supply pump 214, an initial aspiration pressure of the aspiration pump 220, and the threshold value for the concentration of blood are stored in advance.

The computation portion 430 is composed mainly of a CPU and receives inspection information in the inspection units 300, data measured by the sensor S, and the like. The computation portion 430 calculates a switching direction of a flow path switched by the switching unit 150, a supply pressure of the supply pump 214, an aspiration pressure of the aspiration pump 220, and the like based on data read from the storage unit 420 and data received from the input/output portion 410.

A respective control signal based on calculated data is transmitted to each of the switching unit 150, the supply pump 214, the aspiration pump 220, and the inspection units 300. In this manner, when a blood inspection is performed by the inspection units 300, the control unit 400 operates the switching unit 150 for allocation between a state where the main flow path 121 and one bifurcated flow path 131 or the discharge flow path 141 selectively communicate with each other, and a state where the main flow path 121 and a flow path other than the selected one bifurcated flow path 131 or the discharge flow path 141 are blocked from communicating with each other.

Control Method for Blood Inspection System

Figure 2:
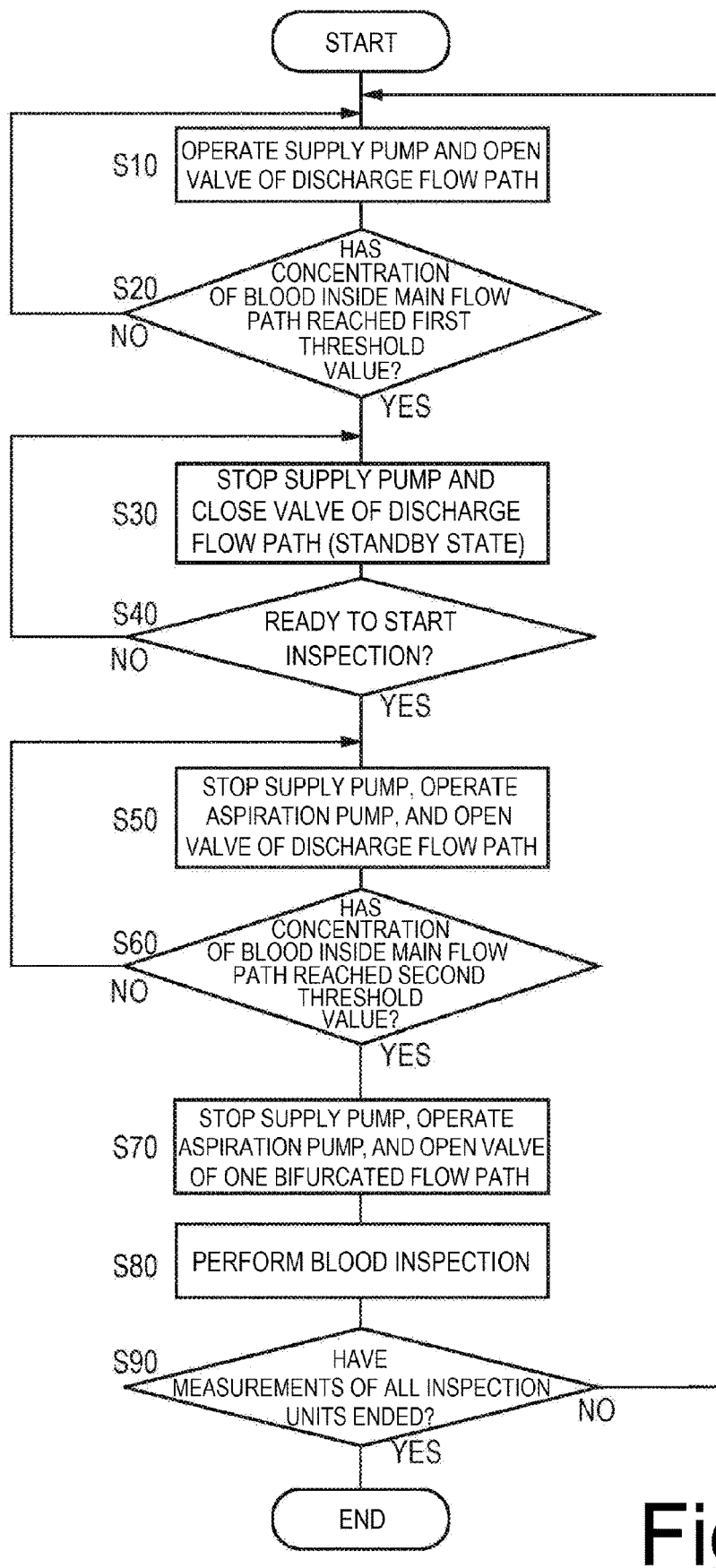
FIG. 2 is a flowchart for describing a control method for a blood inspection system according to the first embodiment.

Hereinafter, a control method for the blood inspection system 10 according to the first embodiment will be described with reference to FIG. 2. FIG. 2 is a view illustrating the control method for the blood inspection system 10 according to the present embodiment.

As illustrated in FIG. 2, generally, the control method for the blood inspection system 10 according to the first embodiment includes a cleaning step of cleaning the insides of the flow paths by filling the main flow path 121 with a flushing liquid (Steps S10 and S20), a standby step of maintaining a standby state until an inspection starts (Steps S30 and S40), a blood replacing step of replacing the inside of the main flow path 121, which was previously filled with the flushing liquid, with blood collected from a living body (Steps S50 and S60), one inspecting step of inspecting blood using one inspection unit 300 (Steps S70 and S80), and another inspecting step of inspecting blood using another unused inspection unit 300 by repeating the steps (Steps S10 to S80) described above (Step S90). A plurality of inspection results are obtained from the plurality of inspection units 300 through the control described above. Hereinafter, each of the steps will be described.

First, in the cleaning step (Steps S10 and S20), the control unit 400 operates the supply pump 214 such that a flushing liquid is supplied to the main flow path 121. At the same time, the control unit 400 operates the switching unit 150 to open a valve causing the main flow path 121 and the discharge flow path 141 to communicate with each other such that a part of a flushing liquid, air, and a residue of blood or the like inside the main flow path 121 are discharged from the discharge flow path 141 to the waste liquid tank T (Step S10). Here, since the switching unit 150 has selected and opened the discharge flow path 141, a valve causing the main flow path 121 and the plurality of bifurcated flow paths 131 to communicate with each other is in a closed state. A flushing liquid is continuously supplied until the inside of the main flow path 121 is replaced with the flushing liquid. If the inside of the main flow path 121 is replaced with the flushing liquid, cleaning the inside of the main flow path 121 is completed.

Here, based on data transmitted from the sensor S, the control unit 400 determines whether or not the inside of the main flow path 121 is replaced with the flushing liquid. Specifically, until the concentration of blood inside the first main flow path 121a measured by the sensor S reaches the first threshold value set in advance, the control unit 400 determines that the inside of the main flow path 121 is not filled with the flushing liquid and continues a cleaning operation (Step S10) (Step S20: NO). If the concentration of blood inside the main flow path 121 reaches the first threshold value set in advance, the control unit 400 determines that the inside of the main flow path 121 is replaced with the flushing liquid and proceeds to a next step (Step S20: YES).

Next, in the standby step (Steps S30 and S40), the control unit 400 stops the supply pump 214, operates the switching unit 150, and closes the valve causing the main flow path 121 and the discharge flow path 141 to communicate with each other (Step S30). Accordingly, the main flow path 121 and other flow paths are blocked from communicating with each other, so that the inside of the main flow path 121 maintains a standby state of being filled with the flushing liquid. Until one inspection starts after the cleaning step (Steps S10 and S20), or until a next inspection starts after one inspection, the control unit 400 stands by while having the inside of the main flow path 121 in a standby state of being filled with the flushing liquid (Step S40: NO). Accordingly, a residue of blood or the like can be inhibited from staying inside the main flow path 121, and a thrombus or the like can be prevented from being formed inside the main flow path 121. When an inspection starts after a predetermined time has elapsed, the control unit 400 proceeds to a next step (Step S40: YES).

When an inspection starts, first, the blood replacing step (Steps S50 and S60) is performed. The control unit 400 stops the supply pump 214 and operates the aspiration pump 220 such that blood is aspirated through the blood collecting needle 110 placed on a living body and the blood is guided into the inside of the main flow path 121. At this time, the control unit 400 maintains an open state of the valve 150 causing the main flow path 121 and the discharge flow path 141 to communicate with each other and causes the flushing liquid inside the main flow path 121 to be discharged to the waste liquid tank T. In addition, the control unit 400 switches the valve 230 to switch the flow of the fluid in the first main flow path 121a from the direction toward the blood collecting needle 110 to the direction toward the aspiration pump 220. Blood is continuously guided until the flushing liquid inside the main flow path 121 is replaced with the blood.

Here, based on data transmitted from the sensor S, the control unit 400 determines whether or not the flushing liquid inside the main flow path 121 is replaced with blood. Specifically, until the concentration of blood inside the main flow path 121 reaches the second threshold value set in advance, the control unit 400 determines that the inside of the main flow path 121 is not replaced with blood and continuously guides blood (Step S60: NO). After the concentration of blood inside the first main flow path 121a measured by the sensor S reaches the second threshold value set in advance, blood is continuously guided for an additional predetermined time (i.e., to ensure that the desired concentration of blood has time to propagate to the third main flow path 121c). Accordingly, if the concentration of blood inside the main flow path 121 reaches the second threshold value, the control unit 400 determines that the flushing liquid inside the main flow path 121 is replaced with blood and proceeds to a next step (Step S60: YES).

Next, in the one inspecting step (Steps S70 and S80), the control unit 400 operates the switching unit 150 while maintaining a state where the supply pump 214 has stopped and the aspiration pump 220 is in operation, thereby opening the valve causing the main flow path 121 and one bifurcated flow path 131 to communicate with each other (Step S70). In the present embodiment, since there are provided eight bifurcated flow paths 131 and eight inspection units 300, one bifurcated flow path 131 is selected from the eight bifurcated flow paths 131.

Next, the control unit 400 performs a clotting inspection of blood which has flowed into the test tube 316, using the clotting time measuring instrument 310 (Step S80). A practitioner disposes the test tube 316, which is in a state of being connected to the bifurcated flow path 131 in advance, in the test tube holding portion M11 of the measuring device M1. If the valve causing the main flow path 121 and one bifurcated flow path 131 to communicate with each other is opened, blood flows into the test tube 316 of one clotting time measuring instrument 310 included in one inspection unit 300, via one bifurcated flow path 131.

Next, the clotting time is measured by driving the measuring device M1. A practitioner inputs data, such as the number and test conditions of the test tubes 316 disposed in the test tube holding portion M11, in advance using the operation unit M15. First, the control unit 400 operates the drive unit M12 such that the test tube 316 into which blood has flowed is excited and the blood and the clotting accelerator 312 are mixed, thereby starting an inspection. Moreover, the drive unit M12 is operated for a rotary movement of the test tube 316 around its cylindrical axis. As clotting of blood proceeds, the viscosity coefficient of blood increases, so that the inspection rod 314 of the test tube 316 gradually starts to make a rotary movement in association with a rotary movement of the test tube 316. Next, the detection unit M13 is operated to detect a rotary movement of the inspection rod 314. The display unit M14 displays a time until a rotary movement of the inspection rod 314 is detected after an inspection starts, as a clotting time. During a clotting inspection of blood, it is preferable to maintain the temperature inside the test tube 316 at approximately 37 degrees, which is close to the body temperature, using a heater or the like.

Next, in another inspection unit is available for performing another inspecting step (Step S90), the control unit 400 returns to the cleaning step (Steps S10 and S20) and the standby step (Steps S30 and S40) to be in a standby state. When another inspection starts, the blood replacing step (Steps S50 and S60) is performed, and the inside of the main flow path 121 is filled with new blood. The inspection unit 300 performs a clotting inspection of blood using this blood.

In the single-use clotting time measuring instrument 310 according to the present embodiment, since blood inside the test tube 316 clots due to an inspection, the same clotting time measuring instrument 310 cannot be reused. Therefore, the control unit 400 operates the switching unit 150 such that a valve for causing the main flow path 121 and another bifurcated flow path 131 to communicate with each other is opened, thereby performing a clotting inspection of blood using an unused inspection unit 300 which has not yet performed an inspection.

The control unit 400 performs the cleaning step (Steps S10 and S20), the standby step (Steps S30 and S40), and the blood replacing step (Steps S50 and S60) for each of the remaining unused inspection units 300 (Step S90: NO). If measurement of all of the inspection units 300 is completed, eight clotting times are obtained as inspection results (Step S90: YES). The display unit M14 collectively displays all of the obtained inspection results. A displaying method is not particularly limited. For example, the times are plotted on the horizontal axis, and the values of the inspection results of the clotting times are plotted on the vertical axis. Accordingly, a practitioner can visually and promptly read a chronological change in the clotting times.

The dosage of an anticoagulant such as heparin to be given to a patient during treatment is adjusted based on the inspection results obtained through the control described above.

As described above, the blood inspection system 10 according to the present embodiment includes the supply section 210, the plurality of inspection units 300, the plurality of bifurcated flow paths 131 which guide blood to the inspection units 300, the aspiration unit 220 which guides the blood to the bifurcated flow paths 131, the discharge flow path 141 which discharges a part of a fluid from the main flow path 121, the switching unit 150 which is capable of selectively switching between the communication state of the main flow path 121 and the plurality of bifurcated flow paths 131 and the communication state of the main flow path 121 and the discharge flow path 141, and the control unit 400 which controls an operation of each of the units of the system. Moreover, the control unit 400 causes the main flow path 121 and one bifurcated flow path 131 of the plurality of bifurcated flow paths 131 to communicate with each other when performing a blood inspection using the inspection units 300 such that blood is guided to one inspection unit 300 of the plurality of inspection units 300, which has not yet performed an inspection.

According to the blood inspection system 10 having such a configuration, it is possible to perform control in which a clotting inspection of blood is performed by selecting one inspection unit 300 from the inspection units 300 which have not yet performed an inspection. Since the clotting time of blood can be automatically and repetitively measured a plurality of times at a desired interval and a desired timing through the control, a chronological change in the clotting time can be measured. In addition, since many of the single-use inspection units 300 can be used, it is possible to perform an inspection more simply in a short time. Accordingly, a thrombus is prevented from being formed and an anticoagulant is prevented from being overdosed, so that a load to a patient can be reduced.

In addition, the discharge flow path 141 is bifurcated from the main flow path 121, and the switching unit 150 switches the main flow path 121 between a state of communicating with one bifurcated flow path 131 of the plurality of bifurcated flow paths 131 and a state of communicating with the discharge flow path 141. In a state where the main flow path 121 and one bifurcated flow path 131 communicate with each other, it is possible to perform a clotting inspection of blood using a selected one of the inspection units 300. In addition, since the main flow path 121 and the discharge flow path 141 are in a state of communicating with each other, the inside of the main flow path 121 can be cleaned by a flushing liquid. Accordingly, the switching unit 150 can easily switch between a state of cleaning the inside of the catheter 100 and a state of performing a blood inspection using the inspection units 300.

In addition, since the blood inspection system 10 further includes the sensor S which measures the concentration of blood included in a fluid inside the main flow path 121, it is possible to easily recognize whether the inside of the main flow path 121 is in a state of being filled with a flushing liquid or in a state of being filled with blood. Accordingly, it is possible to check that cleaning the inside of the catheter 100 is completed and to check the timing to start a clotting inspection of blood.

In addition, since the plurality of inspection units 300 include the clotting time measuring instrument 310 which measures the clotting time of blood guided from the bifurcated flow paths 131, a clotting inspection of blood can be performed more smoothly.

In addition, since the clotting time measuring instrument 310 is a viscosity measuring module which measures the clotting time by measuring the viscosity of blood activated by mixing the clotting accelerator 312, the clotting time can be measured accurately in a shorter time.

The control method for the blood inspection system 10 according to the present embodiment includes the cleaning step of cleaning the inside of the main flow path 121 by discharging a fluid from the main flow path 121 while supplying a flushing liquid to the main flow path 121 (Steps S10 and S20), one inspecting step of inspecting blood using one inspection unit of the plurality of inspection units by causing the main flow path 121 and one bifurcated flow path 131 of the plurality of bifurcated flow paths 131 to communicate with each other (Steps S70 and S80), and another inspecting step of inspecting blood using another inspection unit 300 of the plurality of inspection units 300, which has not yet performed an inspection (Step S90).

According to the control method for the blood inspection system 10 having such a configuration, since air and a residue of blood or the like inside the main flow path 121 can be discharged before an inspection starts, it is possible to collect fresh blood for a blood inspection. In addition, it is possible to perform control in which a clotting inspection of blood is performed by selecting one inspection unit 300 from the inspection units 300 which have not yet performed an inspection. Since the clotting time of blood can be automatically and repetitively measured a plurality of times at a desired interval and a desired timing through the control, a chronological change in the clotting time can be measured. In addition, since the single-use inspection units 300 can be used, it is possible to perform an inspection more simply in a short time. Accordingly, a thrombus is prevented from being formed and an anticoagulant is prevented from being overdosed, so that a load to a patient can be reduced.

Modification Example 1 of Inspection Unit and Measuring Device

Figure 4A:
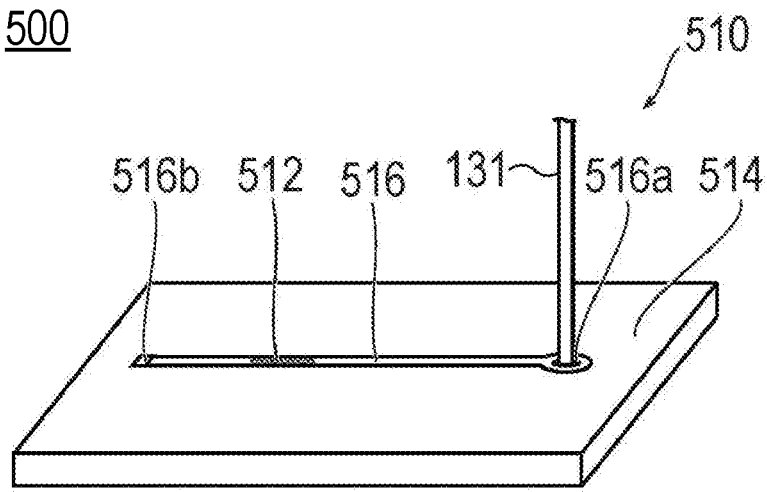
FIG. 4A is a schematic view illustrating an inspection unit according to Modification Example 1.
Figure 4B:
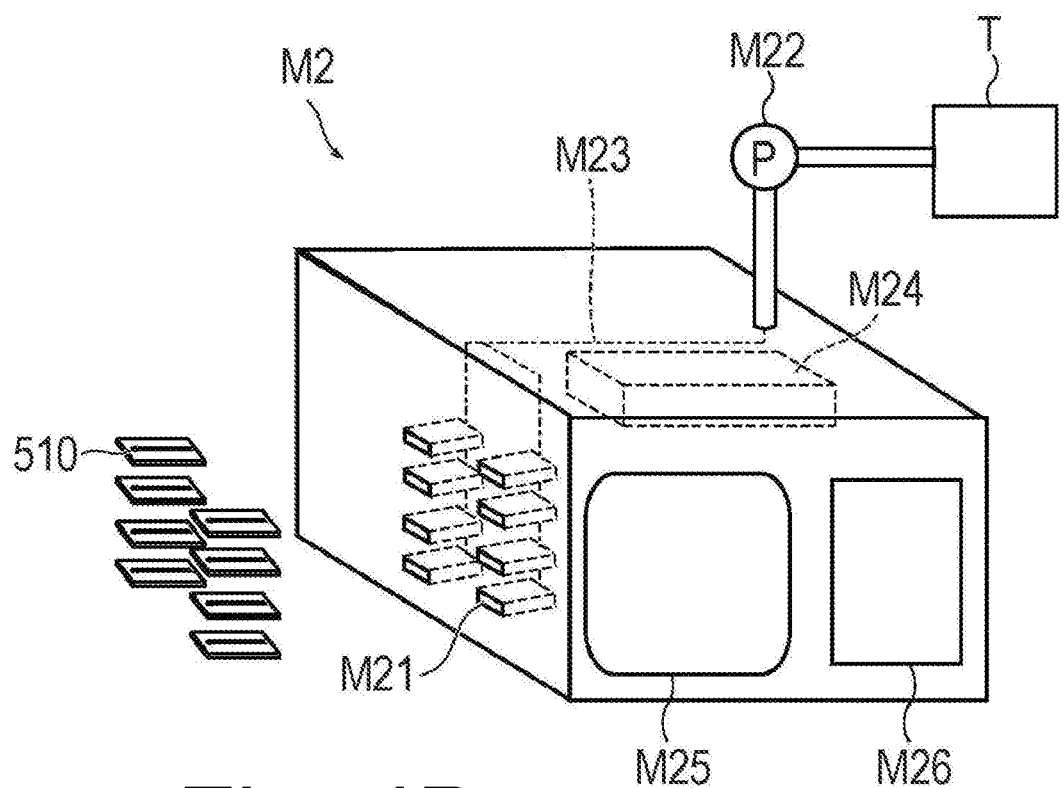
FIG. 4B is a schematic view illustrating a measuring device according to Modification Example 1.

Hereinafter, an inspection unit and a measuring device according to Modification Example 1 will be described with reference to FIGS. 4A and 4B. FIG. 4A is a schematic view illustrating an inspection unit 500 according to Modification Example 1, and FIG. 4B is a schematic view illustrating a measuring device M2 according to Modification Example 1. Since configurations other than the inspection unit 500 and the measuring device M2 are similar to those of the first embodiment described above, the description thereof will be omitted.

The inspection unit 500 includes a clotting time measuring instrument 510. The clotting time measuring instrument 510 is a flow measuring module which measures a clotting time by measuring flow characteristics of blood activated by adding a clotting accelerator and causing the blood to flow.

As illustrated in FIG. 4A, the clotting time measuring instrument 510 according to Modification Example 1 has a clotting accelerator 512 which accelerates clotting of blood by activating the blood, a basal lamella 514 which includes a flat upper surface, and a canaliculus 516 which is disposed on the upper surface of the basal lamella 514 and through which blood can flow.

The clotting accelerator 512 is applied to a part of an inner wall of the canaliculus 516. A member similar to that of the first embodiment described above can be used as the clotting accelerator 512.

The canaliculus 516 includes an inlet port 516a, through which blood can flow in, at one end, and a discharge port 516b, which can discharge blood, at the other end. The inlet port 516a is connected to one bifurcated flow path 131. The discharge port 516b communicates with a drainage flow path M23 (which will be described below). Separately from the canaliculus 516, a tube (not shown), which, for example, communicates with the inlet port 516a and/or the discharge port 516b, measures the viscosity coefficient before blood clots, measures the pressure, and discharges unnecessary blood, may be provided.

The canaliculus 516 is formed of a material which allows blood inside the canaliculus 516 to be recognized from the outside in a visual manner or by a sensor, for example, a material such as a transparent resin or glass.

As illustrated in FIG. 4B, the measuring device M2 includes a plurality of holding portions M21 which hold the plurality of clotting time measuring instruments 510 at respective measurement positions, an aspiration pump M22 which aspirates blood inside the canaliculus 516 from the discharge port 516b, the drainage flow path M23 which causes the discharge port 516b and the aspiration pump M22 to communicate with each other, a detection unit M24 which detects flow characteristics of blood, a display unit M25 which displays a measurement result, and an operation unit M26 with which a practitioner performs a predetermined input operation.

Next, with reference to FIG. 2, a control method for a blood inspection system including the inspection unit 500 according to Modification Example 1 will be described. The control method for a blood inspection system according to Modification Example 1 differs from that of the first embodiment described above in only a step of performing a clotting inspection of blood (Step S80) and is similar thereto in other steps. Accordingly, description thereof will be omitted.

In the step of performing a clotting inspection of blood (Step S80), first, blood flows into the inlet port 516a of the canaliculus 516 via one bifurcated flow path 131. Next, the aspiration pump M22 is operated to aspirate the inside of the canaliculus 516 from the discharge port 516b side, so that blood is drawn into the canaliculus 516 utilizing a suction pressure.

Blood which has flowed into the canaliculus 516 flows from the inlet port 516a toward the discharge port 516b and is mixed with the clotting accelerator 512 disposed in the inner wall of the canaliculus 516. Accordingly, the viscosity of the blood gradually increases, and flow characteristics change. The detection unit M24 is operated to measure the flow characteristics of blood, and the clotting time is measured through analysis processing or the like. The display unit M25 displays the clotting time obtained through the measurement. A configuration in which blood reciprocally flows inside the canaliculus 516 between the inlet port 516a and the discharge port 516b may be employed by providing an aspiration pump on each of the inlet port 516a side and the discharge port 516b side. In addition, similar to the first embodiment described above, during a clotting inspection of blood, it is preferable to uniformly maintain the temperature inside the clotting time measuring instrument 510 at approximately 37 degrees, which is close to the body temperature, using a heater or the like.

As described above, the clotting time measuring instrument 510 of the inspection unit 500 according to Modification Example 1 is a flow measuring module which measures the clotting time by measuring flow characteristics of blood inside the canaliculus 516 in which the clotting accelerator 512 is disposed. Accordingly, the clotting time of blood can be measured more simply in a short time.

Modification Example 2 of Inspection Unit and Measuring Device

Figure 5A:
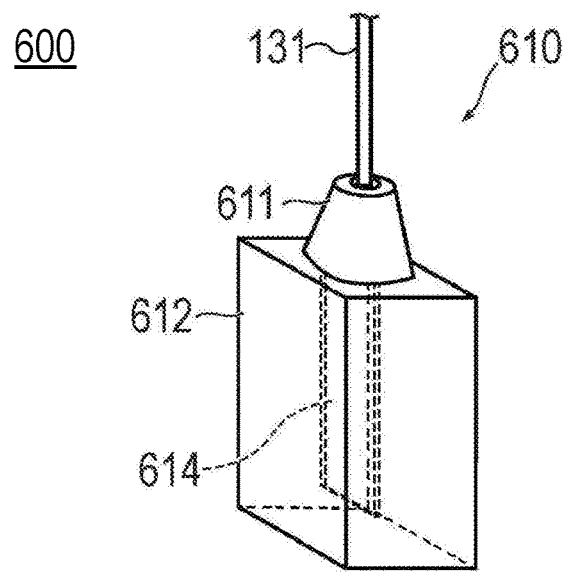
FIG. 5A is a schematic view illustrating an inspection unit according to Modification Example 2.
Figure 5B:
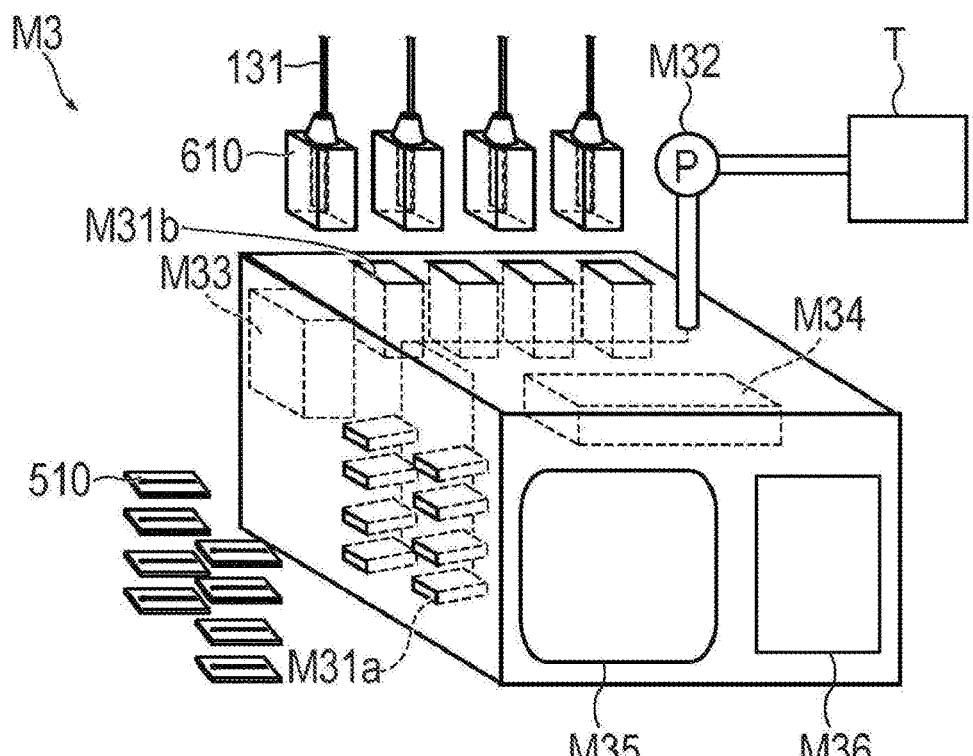
FIG. 5B is a schematic view illustrating a measuring device according to Modification Example 1.

Hereinafter, an inspection unit according to Modification Example 2 will be described with reference to FIGS. 5A and 5B. FIG. 5A is a schematic view illustrating an inspection unit 600 according to Modification Example 2, and FIG. 5B is a schematic view illustrating a measuring device M3 according to Modification Example 2.

In addition to the plurality of clotting time measuring instruments 510 according to Modification Example 1, the inspection unit 600 according to Modification Example 2 further includes a plurality of blood glucose level measuring instruments 610 which measure glucose levels of blood guided from the bifurcated flow paths 131.

The measuring device M3 according to Modification Example 2 functions as both a clotting time measuring device which measures the clotting time of blood, and a blood glucose level measuring device which measures the glucose level of blood. The blood glucose level measuring device will be described with an example of a blood component analysis device which analyzes the components such as glucose contained in blood.

As illustrated in FIG. 5A, the blood glucose level measuring instrument 610 includes a connection section 611 which is connected to the bifurcated flow paths 131, a casing 612 in which the connection section 611 is provided, and a reagent 614 which is disposed inside the casing 612 and contains an exogenous enzyme or a correction liquid.

As illustrated in FIG. 5B, the measuring device M3 includes a plurality of first holding portions M31a and a plurality of second holding portions M31b which respectively hold the plurality of clotting time measuring instruments 510 and the plurality of blood glucose level measuring instruments 610 at measurement positions, an aspiration pump M32 which aspirates blood inside the canaliculus 516 of the clotting time measuring instrument 510 from the discharge port 516b side, a first detection unit M33 which measures a flow of blood inside the canaliculus 516 of the clotting time measuring instrument 510, a second detection unit M34 which measures the glucose concentration of blood, a display unit M35 which displays a measurement result, and an operation unit M36 with which a practitioner performs a predetermined input operation.

The first detection unit M33 has a configuration similar to that of the detection unit M24 according to Modification Example 1 described above. The second detection unit M34 measures the glucose level of blood by measuring a current generated due to electrochemically decomposed hydrogen peroxide which is generated through reaction of glucose in blood, and converting the measured current into a glucose concentration.

As described above, since a blood inspection system according to Modification Example 2 has a configuration similar to that of the first embodiment described above, the clotting time and the glucose level of blood can be automatically and repetitively measured a plurality of times at a desired interval and a desired timing, so that chronological changes in the clotting time and the blood glucose level can be measured.

In addition, the inspection unit 600 according to Modification Example 2 includes the blood glucose level measuring instrument 610 which measures the glucose level of blood guided from the bifurcated flow paths 131. Accordingly, the glucose level of blood can be measured, so that it is possible to perform management in which the blood glucose level approximates to an optimal state during an operation.

Second Embodiment

Figure 6:
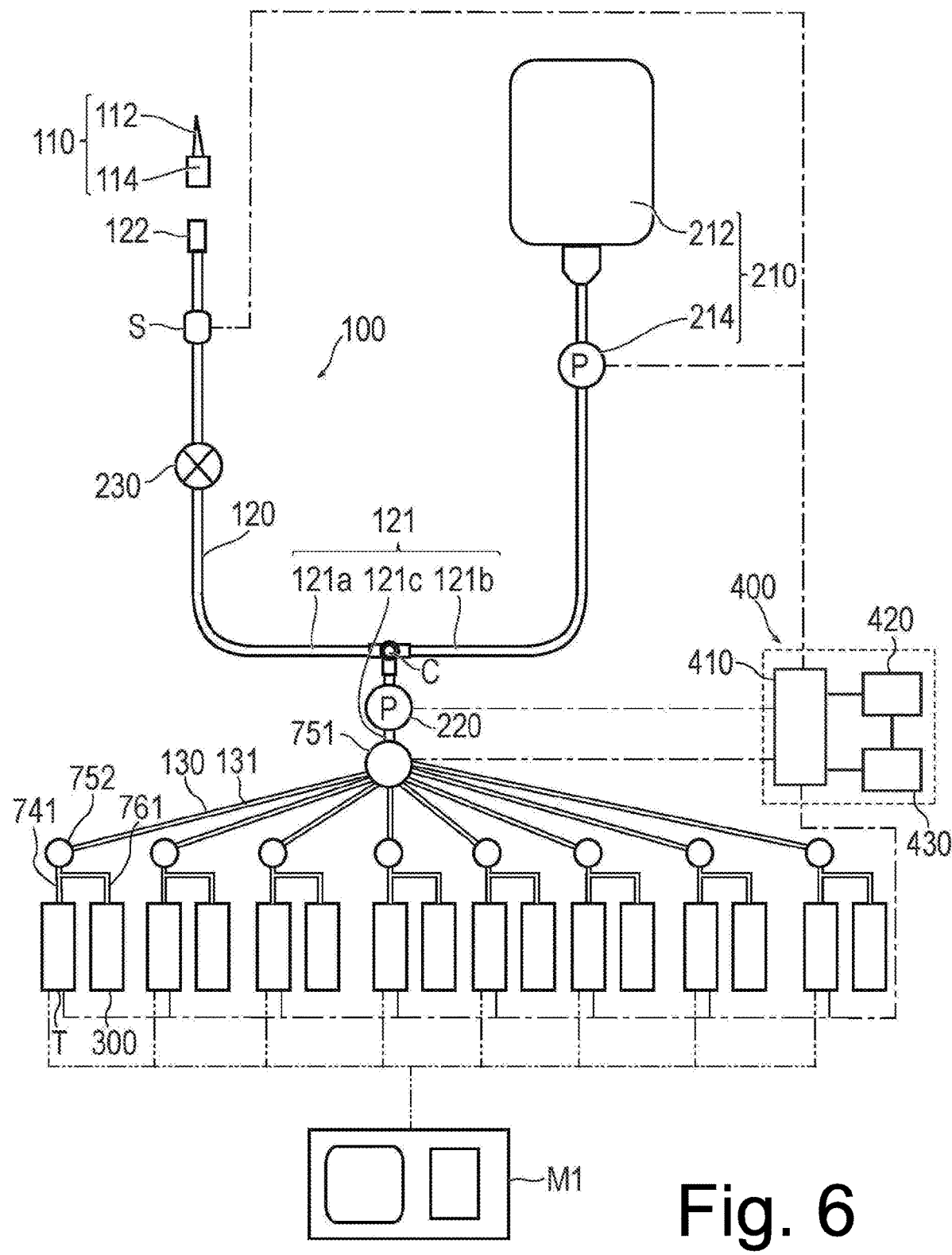
FIG. 6 is a view schematically illustrating the entirety of a blood inspection system according to a second embodiment.

With reference to FIG. 6, a blood inspection system 20 according to a second embodiment will be described. FIG. 6 is a view schematically illustrating the entirety of the blood inspection system 20 according to the second embodiment.

As illustrated in FIG. 6, the blood inspection system 20 according to the second embodiment differs from that of the first embodiment described above in including a plurality of discharge flow paths 741 and a plurality of inspection flow paths 761 which are bifurcated from the bifurcated flow path 131, and two switching units including a first switching unit (corresponding to a primary switching unit) 751 and a second switching unit (corresponding to a secondary switching unit) 752. The same reference signs are applied to parts having the same function as those of the first embodiment described above, and description thereof will be omitted.

The discharge flow paths 741 each have a configuration and a function similar to those of the discharge flow path 141 according to the first embodiment described above and differs from that of the first embodiment described above in that the discharge flow paths 741 are respectively disposed in the bifurcated flow paths 131. Accordingly, the main flow path 121 and the bifurcated flow path 131 are configured to be able to discharge a fluid. The number of the discharge flow paths 741 is the same as the number of the bifurcated flow paths 131.

The inspection flow paths 761 cause the plurality of inspection units 300 and the plurality of bifurcated flow paths 131 to respectively communicate with each other via the second switching unit 752. The inspection flow paths 761 guide blood to the inspection units 300, respectively.

The first switching unit 751 is connected to the main flow path 121 and switches the flow path from the main flow path 121 over to one bifurcated flow path 131. The first switching unit 751 has a configuration and a function similar to those of the switching unit 150 according to the first embodiment described above.

The second switching unit 752 is connected to the bifurcated flow path 131 and switches the flow path from the bifurcated flow path 131 over to the discharge flow path 741 or the inspection flow path 761. Accordingly, the second switching unit 752 guides a fluid, which has been guided to the bifurcated flow path 131, to the discharge flow path 741 or the inspection flow path 761.

As described above, the blood inspection system 20 according to the second embodiment includes the discharge flow paths 741 which discharge at least a part of a fluid from the main flow path 121 and the bifurcated flow path 131, the first switching unit 751 which is capable of selectively switching a communication state of the main flow path 121 and the plurality of bifurcated flow paths 131, and the second switching unit 752 which is capable of selectively switching a communication state of the bifurcated flow path 131 and the discharge flow path 741 or the inspection flow path 761.

According to the blood inspection system 20 having such a configuration, since the bifurcated flow path 131 is divided into the discharge flow path 741 and the inspection flow path 761, blood and fluids other than the blood (e.g., flushing liquid) can be separately guided by the second switching unit 752 with higher accuracy. Accordingly, blood with higher purity can be guided to the inspection unit 300.

Hereinabove, the blood inspection system and the control method for a blood inspection system according to the present invention have been described based on the embodiments and the modification examples. However, the present invention is not limited to only the configurations described in the embodiments and the modification examples and can be suitably changed based on the disclosures in Claims.

For example, a blood inspection performed by the blood inspection system is not limited to a clotting inspection of blood or a component inspection such as measurement of the blood glucose level. The blood inspection thereof widely includes clinical inspections such as a biochemical inspection in which the condition of a disease or the like is examined by utilizing blood.

In addition, the inspection unit is not limited to a configuration including the blood clotting time measuring instrument or the blood glucose level measuring instrument. For example, the inspection unit may be configured to include other measuring instruments such as a blood gas analyzer which measures a lactic acid value, pH or $O_2$, $K^+$ and the like, an electrolyte measuring instrument, and a blood pressure measuring instrument which measures a blood pressure.

In addition, the disposing locations and the number of the supply pumps, the aspiration pumps, and the valves of the blood inspection system are not particularly limited and can be suitably changed.

In addition, the measuring device using the blood glucose level measuring instrument is not limited to a configuration having a function of the blood component analysis device and can have a function of a colorimetric glucose measuring device and the like which analyzes the blood glucose level based on the components such as glucose contained in blood and a change in color of a reacted reagent. The treatment cost can be suppressed by using a single-use reagent which is comparatively inexpensive.

What is claimed is:

1. A blood inspection system for inspecting blood, comprising:
   catheter tubing providing a main flow path for conveying a fluid, wherein the fluid includes blood;
   a supply section comprising a medical bag and a supply pump which supplies a flushing liquid to the main flow path;
   a plurality of inspection units each comprising a container and a measuring instrument configured to perform a blood inspection;
   a plurality of branched flow paths which are bifurcated from the main flow path, wherein each branched flow path guides blood from the main flow path to a respective one of the plurality of inspection units;
   a discharge flow path bifurcated from the main flow path configured to discharge fluid to a discharge tank;
   a switching valve configured to selectively couple the main flow path with a selected one of the plurality of branched flow paths and with the discharge flow path; and
   an aspiration pump which aspirates the fluid from the main flow path and guides the fluid to the switching valve;
   a control unit configured to generate a control signal which is transmitted to the switching valve to set the switching valve to couple the main flow path with a determined one of the branched flow paths configured to perform the blood inspection using a determined one of the plurality of inspection units which is unused.

2. The blood inspection system according to claim 1:
   wherein the discharge flow path is bifurcated from the main flow path by the switching valve separately from the branched flow paths; and
   wherein the switching valve performs switching such that the main flow path is coupled to either one of the branched flow paths or the discharge flow path.

3. The blood inspection system according to claim 1, further comprising:
   a sensor configured to measure a concentration of the blood within the fluid disposed inside the main flow path.

4. The blood inspection system according to claim 1:
   wherein the plurality of measuring instruments each include a clotting time measuring instrument configured to measure a clotting time of the blood respectively guided from the plurality of branched flow paths.

5. The blood inspection system according to claim 4:
   wherein the clotting time measuring instrument is configured to measure the clotting time by measuring a viscosity of the blood mixed with a clotting accelerator.

6. The blood inspection system according to claim 5:
   wherein the clotting time measuring instrument is configured to measure the clotting time by measuring flow characteristics of the blood inside a canaliculus in which the clotting accelerator is disposed.

7. The blood inspection system according to claim 1:
   wherein the plurality of measuring instruments each include a blood glucose level measuring instrument configured to measure a glucose level of the blood respectively guided from the plurality of branched flow paths.

* * * * *